(12) United States Patent  
Chevalier et al.

(10) Patent No.: US 7,676,344 B2
(45) Date of Patent: Mar. 9, 2010

(54) APPARATUS AND METHOD FOR DETERMINING A CHARACTERISTIC RATIO AND A PARAMETER AFFECTING THE CHARACTERISITIC RATIO OF A MULTIPHASE FLUID MIXTURE

(75) Inventors: Philippe Chevalier, Neuilly sur Seine (FR); Gilles Roux, Sainte Genevieve des Bois (FR)

(73) Assignee: Schlumberger Technology Corporation, Sugar Land, TX (US)

( * ) Notice: Subject to any disclaimer, the term of this patent is extended or adjusted under 35 U.S.C. 154(b) by 223 days.

(21) Appl. No.: 11/751,204

(22) Filed: May 21, 2007

(65) Prior Publication Data
US 2007/0287190 A1    Dec. 13, 2007

(30) Foreign Application Priority Data
May 31, 2006    (EP)    ................................. 06290887

(51) Int. Cl.
  *G01N 9/36*    (2006.01)
  *G01N 9/02*    (2006.01)
  *G01N 23/00*    (2006.01)
(52) U.S. Cl. .................. 702/137; 73/32 R; 250/306
(58) Field of Classification Search ................. 702/100, 702/22–23, 25–28, 30, 1, 2, 50, 137; 73/19.01, 73/19.04, 19.1, 32 R, 36, 53.01, 861.04, 861.41, 73/861.63, 23.2, 23.28, 23.38, 23.41, 24.02, 73/24.03, 24.05, 30.01, 30.03; 250/253, 250/255, 306–308, 472.1, 492.1
See application file for complete search history.

(56) References Cited

U.S. PATENT DOCUMENTS

| | | | | |
|---|---|---|---|---|
| 6,265,713 | B1 * | 7/2001 | Berard et al. | 250/269.3 |
| 6,335,959 | B1 * | 1/2002 | Lynch et al. | 378/45 |
| 6,405,604 | B1 * | 6/2002 | Berard et al. | 73/861.63 |
| 7,469,188 | B2 * | 12/2008 | Wee | 702/45 |
| 2004/0046115 | A1 * | 3/2004 | Berard et al. | 250/256 |

FOREIGN PATENT DOCUMENTS

| | | |
|---|---|---|
| EP | 0069679 | 1/1983 |
| GB | 2316167 | 2/1998 |
| WO | WO9742493 | 11/1997 |
| WO | WO9910712 | 3/1999 |
| WO | WO0250522 | 6/2002 |

OTHER PUBLICATIONS

Fitzgerald et al., Continuous Gamma-Ray Densitometry in a Borehole Flow Meter, 2004 IEEE, pp. 732-736.*

* cited by examiner

*Primary Examiner*—Michael P. Nghiem
*Assistant Examiner*—Toan M Le
(74) *Attorney, Agent, or Firm*—Darla P. Fonseca; Jaime Castano (57) ABSTRACT

An apparatus and method is presented for controlling the quality of a mass density measurement of a multiphase fluid mixture including a plurality of fluid fractions and a plurality of constituting elements. The method includes the steps of: submitting a measuring pipe to a flux of high energy photons and measuring count rates; determining a mass density of the multiphase fluid mixture based on count rate measurements in a first and second energy windows; determining an electronic density of the multiphase fluid mixture based on count rate measurements in a third energy window; and comparing the electronic density to the mass density of the multiphase fluid mixture.

10 Claims, 7 Drawing Sheets

APPARATUS AND METHOD FOR DETERMINING A CHARACTERISTIC RATIO AND A PARAMETER AFFECTING THE CHARACTERISITIC RATIO OF A MULTIPHASE FLUID MIXTURE

FIELD OF THE INVENTION

An aspect of the invention relates to a method for controlling the quality of a mass density measurement of a multiphase fluid mixture. The measurements are made with a multi-energy photon densitometer. The mass density is used in the calculation of a fluid mixture characteristic ratio, e.g. the water liquid ratio.

Another aspect of the invention relates to a method for determining an actual value of the fluid mixture characteristic ratio and an actual value of a parameter affecting the fluid mixture characteristic ratio of a multiphase fluid mixture. A further aspect of the invention relates to a measuring apparatus implementing such a method.

BACKGROUND OF THE INVENTION

The documents WO 99/10712 and WO 02/50522 describe a method and apparatus for measuring fluid mixture (oil effluent made of water, oil and gas) flow rates. The apparatus comprises a Venturi, a pressure sensor comprising pressure takeoffs opening out into a measuring section of the Venturi, a temperature sensor, a source and a detector of gamma rays positioned on opposite sides of a throat of the Venturi. The source and the detector enable determining the density and the composition of the fluid mixture. The detector measures the attenuation of the gamma rays having passed through the fluid mixture in two different energy levels. The energy levels are such that the high energy count rate is essentially sensitive to the density of the fluid mixture, and the low energy count rate is also sensitive to the composition of the fluid mixture. The measurements of pressure and temperature enable determining the gas density and the gas flow rate under flow rate condition and normal conditions of pressure and temperature, respectively. The apparatus enables measuring the total mass flow rate, the water/liquid mass ratio, and the oil, water and gas flow rates. There is a risk of significant variation of the low energy water mass attenuation coefficients with the presence of salt species (e.g. NaCl, KCl, etc. . . . ) or other heavy atoms (e.g. H2S, CO2, etc. . . . ), as the concentration of salt species and heavy atoms may vary during the measurements. This variation in compositional elements has an impact, in particular on the water-liquid ratio measurement accuracy as measured with the prior art apparatuses and methods.

For example, the low energy mass attenuation coefficient for pure water is $0.03334$ $m^2/kg$ and for water with 25% NaCl by mass is $0.05474$ $m^2/kg$, thus corresponding to a difference of around $0.02000$ $m^2/kg$. Further, in order to achieve an absolute error on the water liquid ratio inferior to ±0.05, it is necessary to know the low energy water mass attenuation coefficient with an accuracy better than ±0.00015 $m^2/kg$. In applications where the water salinity may change with time, the low energy water mass attenuation coefficient needs to be monitored and updated. However, in the example of permanent sub sea applications, accuracy is difficult to maintain because liquids sampling is not regularly feasible and the measuring apparatus is not accessible for long periods of time.

SUMMARY OF THE INVENTION

It is an object of the invention to propose an apparatus and a method for controlling the quality of a mass density measurement used in the calculation of a fluid mixture characteristic ratio of a multiphase fluid mixture, e.g. the water liquid ratio, and an apparatus and method for determining a corrected value of said characteristic ratio and a corrected value of a parameter affecting said characteristic ratio of a multiphase fluid mixture that overcomes at least one of the drawbacks of the prior art.

The invention proposes a method using three energy peaks of the spectrum of a high energy photon source (as an example, the peaks at 32 keV, 81 keV and 356 keV of a Barium 133 gamma source) in order to compute directly the electronic density of the multiphase fluid mixture using the higher energy peak (356 keV). This enables calculating a complementary measurement to the dual-energy gamma measurement of the prior art. According to another aspect of the invention, this method enables determining a parameter affecting the fluid mixture characteristic ratio (as an example, water salinity affecting the water liquid ratio) and an actual characteristic ratio of the multiphase mixture. The invention enables ensuring a redundancy in the measurements and therefore a quality control of the measurements in real time.

According to a first aspect, the invention relates to a method for controlling the quality of a mass density measurement of a multiphase fluid mixture comprising a plurality of fluid fractions and a plurality of constituting elements. The method comprises the steps of:

submitting a measuring pipe to a flux of gamma photons, and measuring count rates, the measuring pipe being arranged to let the gamma photons pass through the multiphase fluid mixture, determining a mass density of the multiphase fluid mixture based on count rate measurements in a first and second energy window, the first and second energy windows being chosen so that the measurements in said energy windows are mainly sensitive to the fluid fractions and the constituting elements, determining an electronic density of the multiphase fluid mixture based on count rate measurements in a third energy window, the third energy window being chosen so that the measurements in the third energy window are substantially sensitive to the density of the constituting elements, and comparing the electronic density to the mass density of the multiphase fluid mixture, one of said densities being corrected with a factor depending on the atomic number and the mass number of the multiphase fluid mixture prior to comparison, a difference between both densities indicating the quality of the mass density measurement of the multiphase fluid mixture.

The mass density may be determined by:

measuring a first and a second count rates in the first energy window when the measuring pipe is empty and when the multiphase fluid mixture is passed through the measuring pipe, respectively, measuring a first and a second count rates in the second energy window when the measuring pipe is empty and when the multiphase fluid mixture is passed through the measuring pipe, respectively, and calculating the mass density of the multiphase fluid mixture based on the first and second count rates in the first and second energy windows.

The electronic density may be determined by:

measuring a first and a second count rates in the third energy window when the measuring pipe is empty and when the multiphase fluid mixture is passed through the measuring pipe, respectively, and calculating the electronic density of the multiphase fluid mixture based on the first and second count rates in the third energy window, and a measuring pipe geometry dependent factor.

According to a further aspect, the invention relates to a method for determining an actual value of a fluid mixture characteristic ratio and an actual value of a parameter affecting the characteristic ratio of a multiphase fluid mixture, the multiphase fluid mixture comprising a plurality of fluid fractions, at least one fraction density being affected by the actual value of the parameter. The method comprises a plurality of steps. An initial reference measurement step comprises determining an initial value of the parameter affecting the characteristic ratio of the multiphase fluid mixture, and determining reference values for each phase of the multiphase fluid mixture by submitting the measuring pipe to a flux of photons and measuring count rates, each phase being passed one at a time in the measuring pipe during this step. A measuring step comprises applying the method for controlling the quality of a mass density measurement of the multiphase fluid mixture according to the invention. When the quality is acceptable, a first characteristic ratio determination step comprises determining the actual value of the characteristic ratio based on the initial value of the parameter affecting the characteristic ratio, the reference values and the mass density measurement. When the quality is unacceptable, a second characteristic ratio determination step comprises determining a first value of the characteristic ratio based on the electronic density of the multiphase fluid mixture, an electronic density of a first fraction (e.g. the liquid fraction), an electronic density of a second fraction (e.g. the water fraction), and determining a second value of the characteristic ratio based on the value of the parameter affecting the characteristic ratio, the reference values and the mass density measurement. Then, the first is compared to the second value of the characteristic ratio. Subsequently, a variation of the parameter is applied by incrementing the parameter when the first value of the characteristic ratio is not substantially equal to the second value of the characteristic ratio, and repeating the determination of the first and second value of the characteristic ratio based on the incremented parameter. Then, the actual value of the characteristic ratio and the actual value of the parameter affecting the characteristic ratio is determined when the first value of the characteristic ratio is substantially equal to the second value of the characteristic ratio.

The characteristic ratio may be the water liquid ratio, the gas oil ratio, or the gas liquid ratio.

Advantageously, the density of the fraction affected by the parameter may be obtained from a look-up table.

According to still a further aspect, the invention relates to a measuring apparatus comprising a measuring pipe arranged to let pass a multiphase fluid mixture, a source emitting high energy photons into a plurality of energy levels though the measuring pipe, a detector of photons receiving the photons attenuated by the multiphase fluid mixture, and an electronic arrangement coupled to the detector. The electronic arrangement comprises a processor and a memory and is arranged to perform the determination and calculation steps of the method according to the invention.

The invention enables using the direct electronic mixture density measurement, based on count rate measurements in a high energy window (such as 356 keV of Barium), without needs of fluids or reference measurements, to track and correct for changes in the fluid mixture density computation model that is using phase fractions calculated from count rates in two lower energy windows (such as 32 keV and 81 keV of Barium) and with monophasic fluids densities entered at standard conditions and recomputed at line conditions using PVT correlation. By comparing the density calculated from count rates in the high energy window (such as 356 keV of Barium) and the density calculated from count rates in two lower energy windows (such as 32 keV and 81 keV of Barium), it is possible to identify changes that may be caused either by changes in composition of one or more of the phases, or by inaccurate PVT calculations.

With the invention, it is possible to determine the water liquid ratio even if the water liquid ratio decreases substantially.

Further, the invention enables determining the water liquid ratio without any need of regularly sampling and analyzing water, thus eliminating the problems linked to sampling (difficult to implement in particular application, water not separating properly due to emulsions, water contaminated by droplets of oil that have not separated, etc. . . . ).

These and other aspects of the invention will be apparent from and elucidated with reference to the embodiments described hereinafter.

BRIEF DESCRIPTION OF THE DRAWINGS

The present invention is illustrated by way of example and not limited to the accompanying figures, in which like references indicate similar elements.

DETAILED DESCRIPTION OF THE INVENTION

Figure 1:
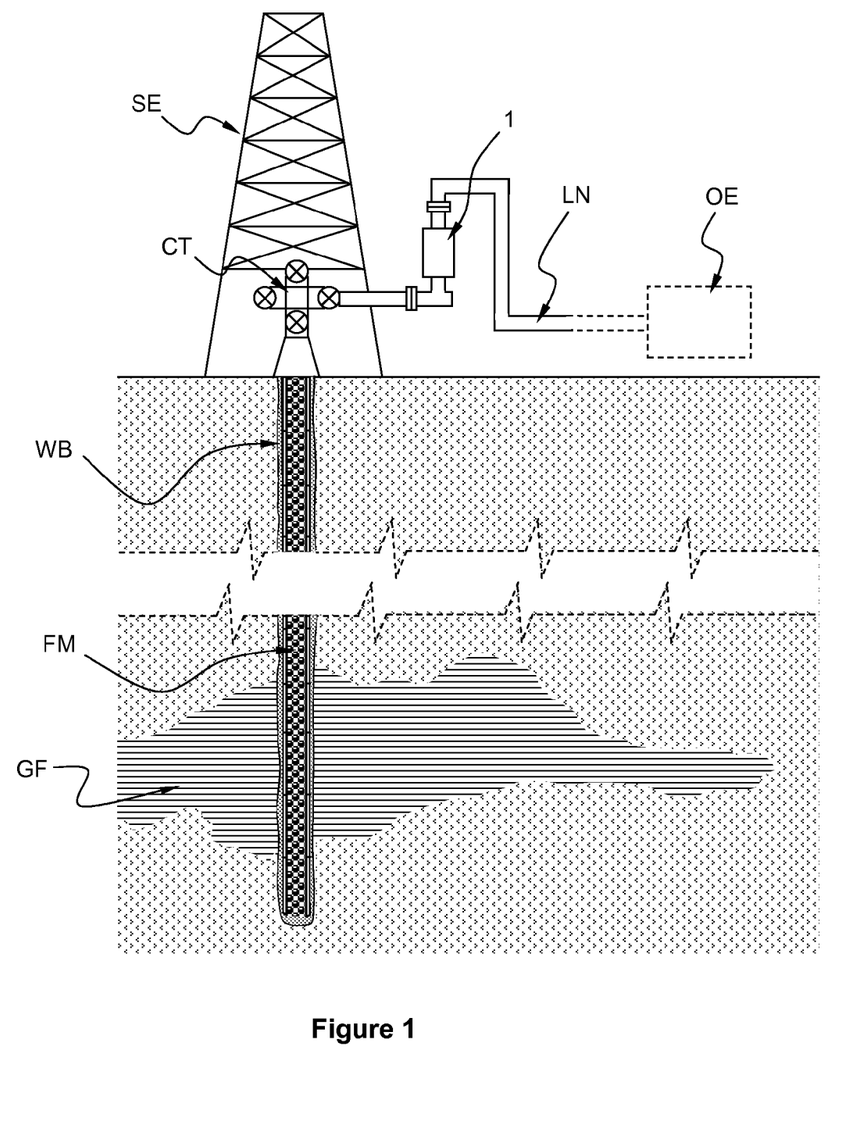
FIG. 1 schematically represents a typical on-shore hydrocarbon well location.

FIG. 1 shows, in a highly schematic manner, a typical onshore hydrocarbon well location and surface equipments SE above a hydrocarbon geological formation GF after a well-bore WB drilling operation has been carried out, after a casing string has been run, after cementing operations have been carried out and exploitation has begun.

A fluid mixture FM flows from selected zones of the hydrocarbon geological formation GF out of the well from a well head CT. The well head is coupled to other surface equipment OE by a flow line LN. The surface equipment OE may typically comprise a chain of elements connected together (e.g. a pressure reducer, a heat exchanger, a burner, etc. . . . ). An apparatus 1 which is typically coupled to the flow line LN measures a multiphase fluid mixture FM flow rates.

The fluid mixture FM is a multiphase fluid mixture comprising a plurality of fluid fractions (water, oil, gas) and a plurality of constituting elements (water, various hydrocarbon molecules, various molecules solved in water).

Figure 2:
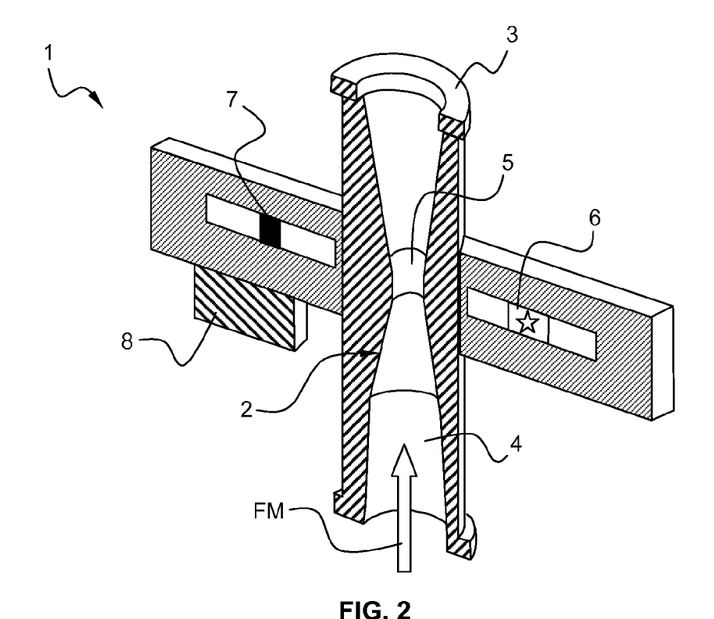
FIG. 2 is a cross-section and perspective view into a measuring apparatus according to the invention.

FIG. 2 diagrammatically shows the apparatus 1 for measuring a multiphase fluid mixture FM flow rates. The apparatus 1 comprises a pipe section 3 which internal diameter gradually decreases from an upstream part 4 to a throat 5, forming a convergent Venturi 2. The convergent Venturi induces a pressure drop between the upstream part 4 and the throat 5. The pipe section 3 can be coupled to any flowing line LN by any appropriate coupling arrangement (not shown).

The apparatus 1 comprises a plurality of pressure sensors (not shown) for measuring a pressure of the multiphase fluid mixture FM, and a pressure drop due to the convergent Venturi. The apparatus 1 also comprises a temperature sensor (not shown) for measuring the temperature of the fluid mixture FM. The measurements of the pressure and the temperature enable the determination of the pressure and temperature of the flowing fluid mixture FM.

The apparatus 1 further comprises a source 6 and a detector 7 for measuring the density and fractions of the fluid mixture FM. The source 6 and the detector 7 are diametrically positioned on each opposite sides of the throat 5 in appropriate blocks coupled to the pipe section 3.

Figure 3:
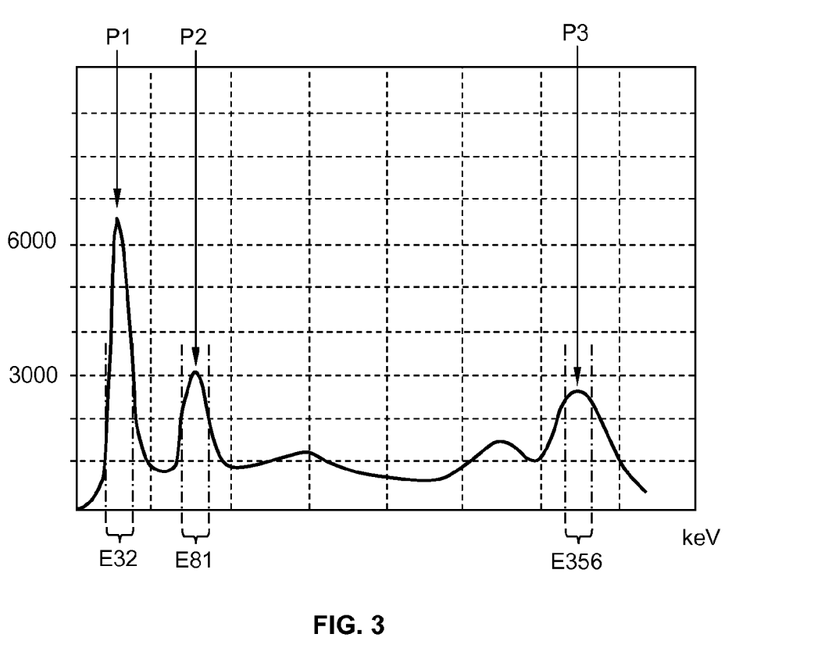
FIG. 3 shows typical gamma ray emission or detection spectra (measured count rates as a function of energy) of a measuring apparatus according to the invention.

The source 6 is a photons producing source, for example a gamma-X photons source or an X-ray source. Preferably, the source produces photons at least three different energy levels (two low energy levels and a high energy level). For example, as shown in FIG. 3, the source is made of the radioisotope Barium 133 producing gamma photons. The energies of the photons are distributed in a spectrum with several peaks P1, P2, P3, a first peak P1 at a low energy around 32 keV, a second peak P2 at a low energy around 81 keV and a third peak P3 at a high energy around 356 keV. Alternatively, a known X-Ray tube may be used as a source.

The detector 7 comprises a scintillator crystal (e.g. NaITl) and a photomultiplier. The detector measures the count rates in the various energy windows corresponding to the attenuated gamma rays having passed through the fluid mixture. Energy windows E32, E81, E356 in which count rates are measured are associated to the peaks in the energy spectrum of the gamma photons P1, P2, P3, respectively. The detector provides three series of signals, representative of the numbers of photons detected in the first energy window E32, the second energy window E81 and the third energy window E356.

The first E32 and second E81 energy windows are such that the measurements in these energy windows are mainly sensitive to the fluid fractions of fluid mixture and the constituting elements (composition) due to the photoelectric and Compton effects at these energies. The third energy window E356 is such that the measurements in this energy window are substantially sensitive to the density of the constituting elements due to the Compton effect only at this energy.

Preferably, the blocks coupled to the pipe receiving the source and the detector comprise appropriate windows into the flow (not shown) made of a material showing low absorption of the gamma rays in the energy windows of interest.

The pressure sensors, the temperature sensor and the detector are all coupled to an electronic arrangement 8. The electronic arrangement 8 determines the flow rates of the individual phases of the multiphase fluid mixture, the water liquid ratio and other values based on measurements provided by the sensors and the detector.

Figure 4:
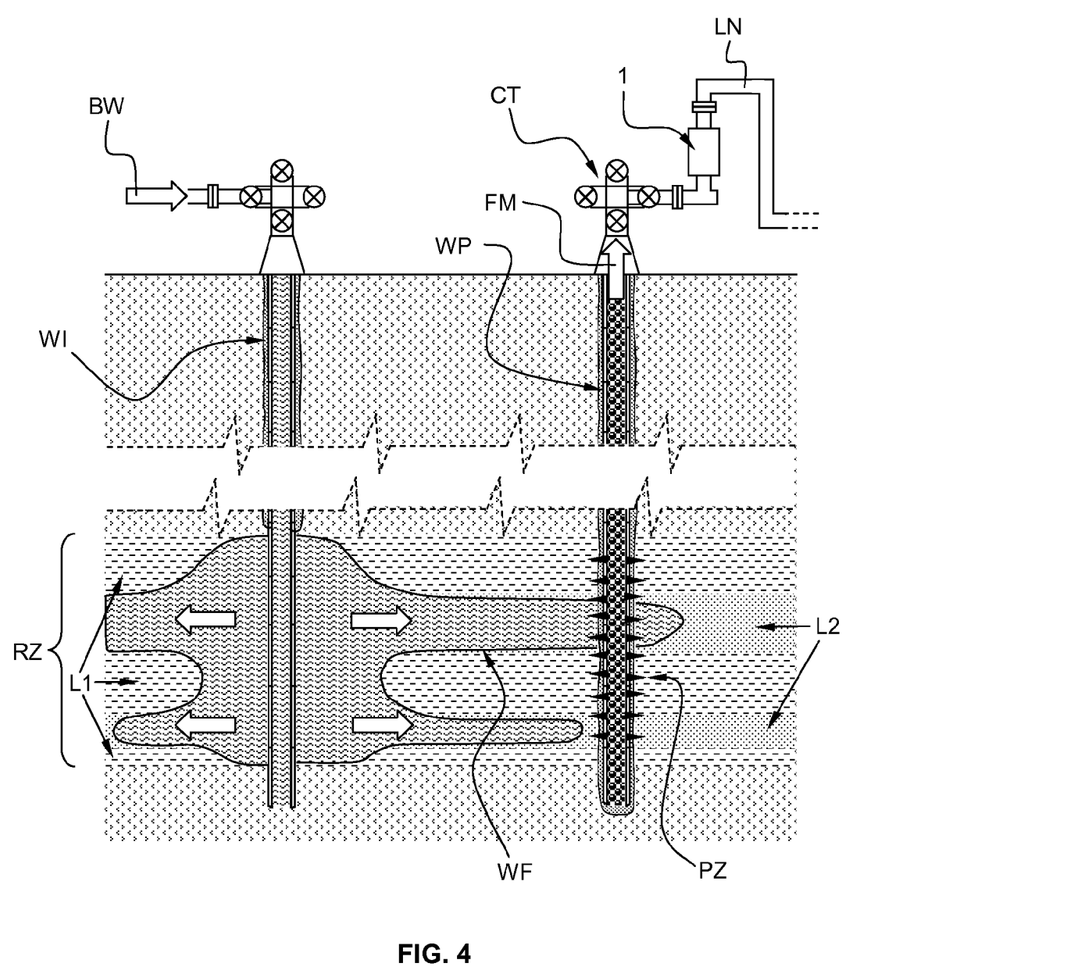
FIG. 4 schematically represents an on-shore hydrocarbon well location in which salinity varies.

FIG. 4 shows in a highly diagrammatic manner an on-shore hydrocarbon well location which illustrates a typical example where salinity of the multiphase fluid mixture may vary. In this application, an injector well WI and a producer well WP have been previously drilled and cased. The producer well WP has been further perforated PZ along a reservoir zone RZ. The injector and producer wells are forming a water drive zone. As water BW is being injected and displaced outside the injector well, the shape of interface between oil and water is expected to alter. The waterfront WF is moving forward inside the reservoir rocks and is pushing the oil towards the producer well WP. That results in a better drainage of the reservoir. Typically, in case of a reservoir having heterogeneous permeability, the front advancement is non-uniform. The water will preferentially progress in layers or zones having a high permeability L2, whereas other layers or zones will remain non-flushed L1. The waterfront might be heterogeneous and exhibit some fingering due to forerunners progressing faster in highly permeable layers L2. Further, generally, the water BW injected into the injector well WI is the water available at the well location, namely often brine water. Thus, when the waterfront WF reaches the producer well WP, the water liquid ratio and the salinity of the water phase in the multiphase fluid mixture FM produced will vary. The salinity may be affected by various salts, for example NaCl, KCl, $CaCl_2$, $MgSO_4$, etc. . . . , or combinations of different salt species. The example described hereinbefore focused on the influence of salinity on the multiphase fluid mixture. However, other constituents (for example $H_2S$, $CO_2$, Sulphur, etc. . . . ) may have an influence on the multiphase fluid mixture, thus affecting the quality of computation of the water liquid ratio of the multiphase fluid mixture made by the apparatus as previously described.

Figure 5:
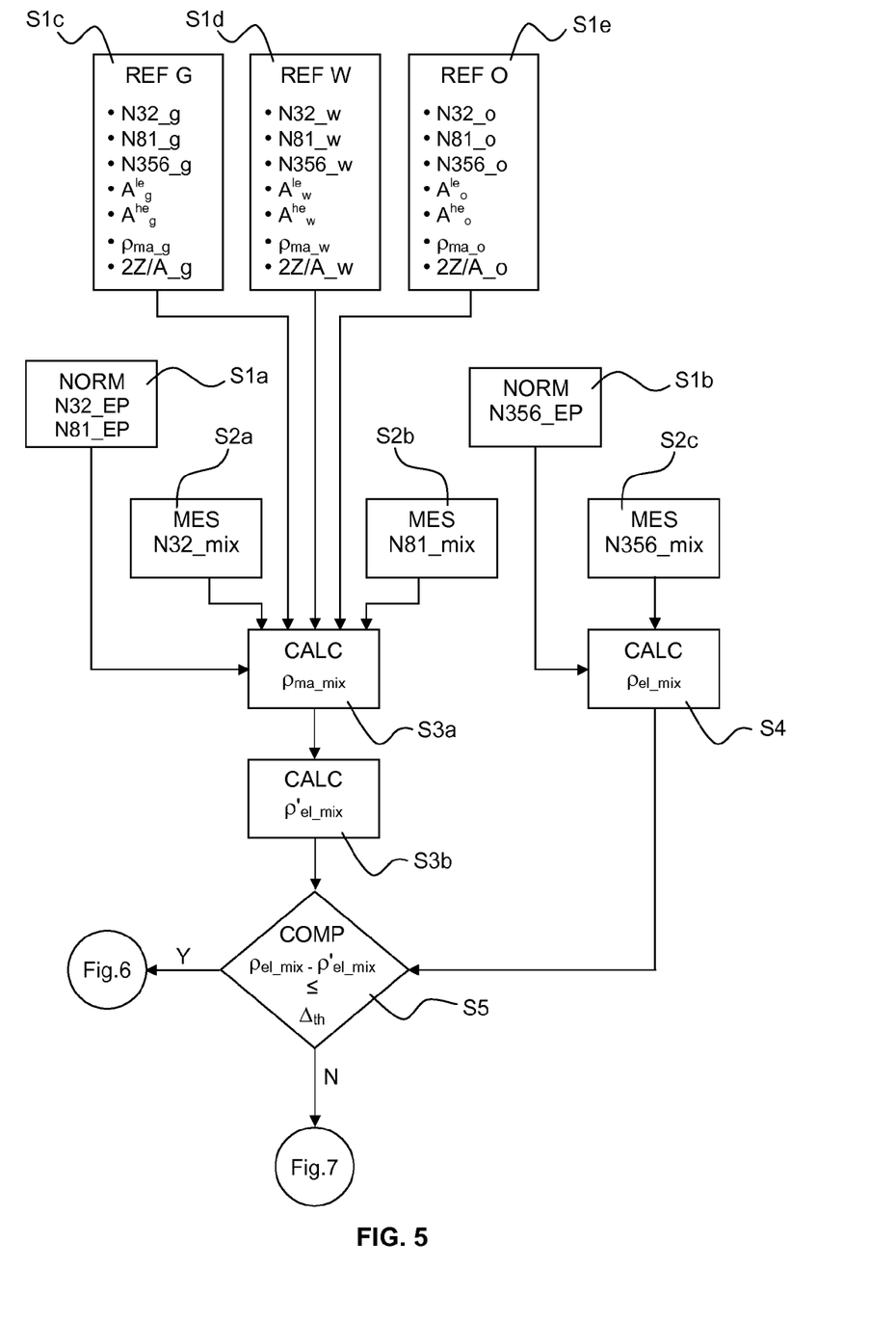
FIG. 5 is a diagram illustrating a method for controlling the quality of a mass density measurement of a multiphase fluid mixture according to the invention.

FIG. 5 is a diagram illustrating a method for controlling the quality of a mass density measurement of a multiphase fluid mixture according to the invention, said mass density measurement being used in the calculation of the water liquid ratio. In a first step S1a and S1b, various normalization measurements NORM are performed. These normalization measurements consist in measuring first count rates N32_EP in the first energy window E32, first count rates N81_EP in the second energy window E81 (Step S1a), and first count rates N356_EP in the third energy window E356 (Step S1b) when the measuring pipe is empty. Practically, these normalization measurements can be performed one time, for example before installation of the apparatus 1 onto the line LN but after installation of the source into the source block of the apparatus. Normalization measurements can be made with air in the measuring pipe. Advantageously, a correction regarding normal condition of pressure and temperature can be applied to these normalization measurements. In further steps S1c, S1d and S1e, various reference measurements REF G, REF W and REF O are performed. The reference measurement REF G (Step S1c) consists in determining count rates N32_g in the first energy window E32, count rates N81_g in the second energy window E81, count rates N356_g in the third energy window E356, attenuations at 32 keV $A^{le}_g$ and at 81 keV $A^{he}_g$, and the ratio between the atomic number and the mass number 2Z/A_g for a reference mixture comprising 100% of gas (fractions $\alpha_g=1$, $\alpha_w=\alpha_o=0$). The reference measurement REF W (Step S1d) consists in determining count rates N32_w in the first energy window E32, count rates N81_w in the second energy window E81, count rates N356_w in the third energy window E356, attenuations at 32 keV $A^{le}_w$ and at 81 keV $A^{he}_w$, and the ratio between the atomic number and the mass number 2Z/A_w for a reference mixture comprising 100% of water (fractions $\alpha_w=1$, $\alpha_g=\alpha_o=0$). The reference measurement REF O (Step S1e) consists in determining count rates N32_o in the first energy window E32, count rates N81_o in the second energy window E81, count rates N356_o in the third energy window E356, attenuations at 32 keV $A^{le}_o$ and at 81 keV $A^{he}_o$, and the ratio between the atomic number and the mass number 2Z/A_o for a reference mixture comprising 100% of oil (fractions $\alpha_o=1$, $\alpha_w=\alpha_g=0$).

In a second step S2a, S2b, S2c, various measurements MES are performed. These measurements consist in measuring second count rates N32_mix in the first energy window E32 (Step S2a), second count rates N81_mix in the second energy window E81 (Step S2b), and second count rates N356_mix in the third energy window E356 (Step S2c) when the multiphase fluid mixture is passed through the measuring pipe. Practically, these measurements are performed continuously or regularly once the apparatus 1 is installed on the line LN.

In a third step S3a, the mass density $\rho_{ma\_mix}$ of the multiphase fluid mixture is calculated based on the first N32_EP, N81_EP and second N32_mix, N81_mix count rates in the first E32 and second E81 energy windows. The mass density $\rho_{ma\_mix}$ calculation is based on the knowledge of the fluid density of each phase (obtained during fluid reference measurements), recomputed at line conditions (using PVT correlations) and with the relative volume fractions of these phases. This calculation has been described in details in several documents, in particular WO 02/50522. Further, in a step S3b, the electronic density $\rho'_{el\_mix}$ associated to the mass density $\rho_{ma\_mix}$ of the multiphase fluid mixture is determined. The electronic density $\rho'_{el\_mix}$ associated to the mass density $\rho_{ma\_mix}$ of the multiphase fluid mixture is a corrected value taking into account the atomic number Z and the mass number A of the multiphase fluid mixture, namely:

$$\rho'_{el\_mix} = \rho_{ma\_mix} \times \left(\frac{2Z}{A}\right)_{mix}$$

The atomic number Z and the mass number A are determined by a compositional characterization of the multiphase fluid mixture issued from samples that have been taken for example before installing the measuring apparatus.

In a fourth step S4 the electronic density $\rho_{el\_mix}$ of the multiphase fluid mixture is determined. The electronic density $\rho_{el\_mix}$ is calculated based on the first N356_EP and second N356_mix count rates in the third energy window E356, and a factor K, namely:

$$\rho'_{el\_mix} = K \times \ln\left(\frac{N356\_mix}{N356\_EP}\right)$$

The factor K is depending on the measuring pipe geometry. It is determined by calibration.

In a fifth step S5, the corrected electronic density $\rho'_{el\_mix}$ (i.e. the associated mass density $\rho_{ma\_mix}$) is compared to the electronic density $\rho_{el\_mix}$. As an example, the comparison may consist in calculating the difference between both electronic density $\rho_{el\_mix}$ and $\rho'_{el\_mix}$ and compare this difference to a threshold value $\Delta_{th}$.

When the difference is lower than the threshold value (branch Y), it is an indication that the measurements made by the apparatus can be validated. As a consequence, the water liquid ratio can be calculated based on the calculation as explained hereinafter in connection with FIG. 6.

Comparing the electronic densities is advantageous because the electronic density $\rho_{el\_mix}$ is the result of direct measurements requiring only a normalization and independent of any calibration or reference measurements.

When the difference is higher than the threshold value (branch N), it is an indication that the measurements made by the apparatus are incorrect, for example due to variation in the multiphase fluid mixture composition. As a consequence, the water liquid ratio can be calculated based on a correction method taking into account the evolution of a parameter PRM influencing the fluid mixture characteristic ratio (e.g. water liquid ratio) as explained hereinafter in connection with FIG. 7.

Thus, the comparison is an indicator of the quality of the mass density measurement of the multiphase fluid mixture that can be used in the subsequent determination of a fluid mixture characteristic ratio, for example the water liquid ratio.

As an alternative, the comparison may consist in calculating a ratio between the determined densities and compared this ratio to a threshold value.

Figure 6:
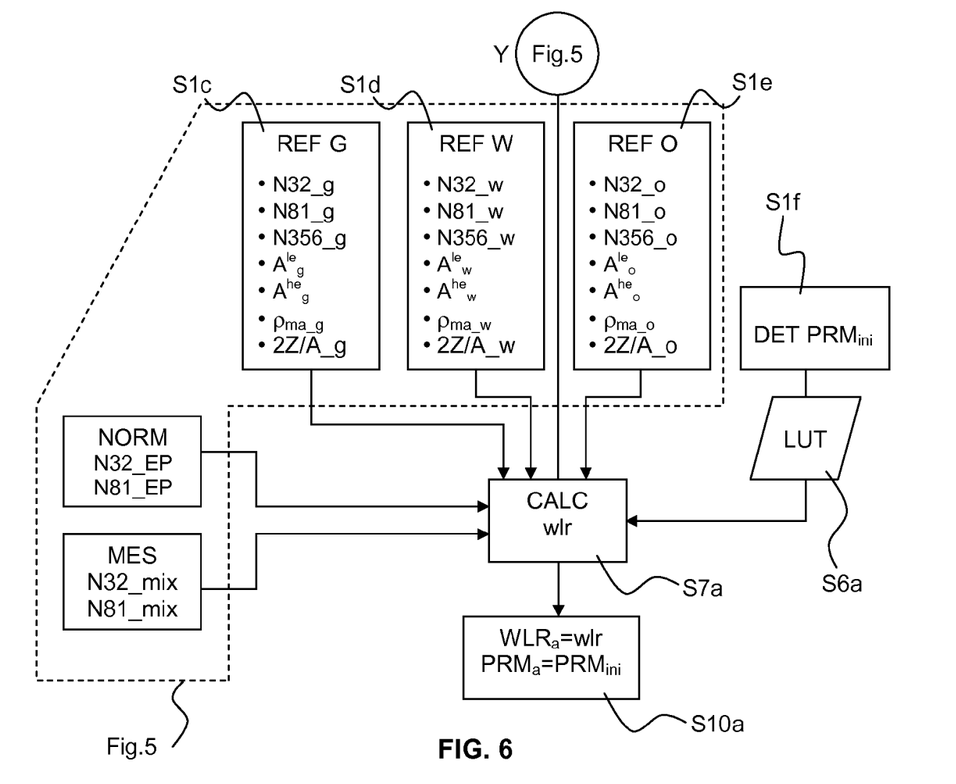
FIGS. 6 and 7 are diagrams illustrating a method for determining a corrected value of a water liquid ratio and a corrected value of a parameter affecting the water liquid ratio of a multiphase fluid mixture according to the invention.
Figure 7:
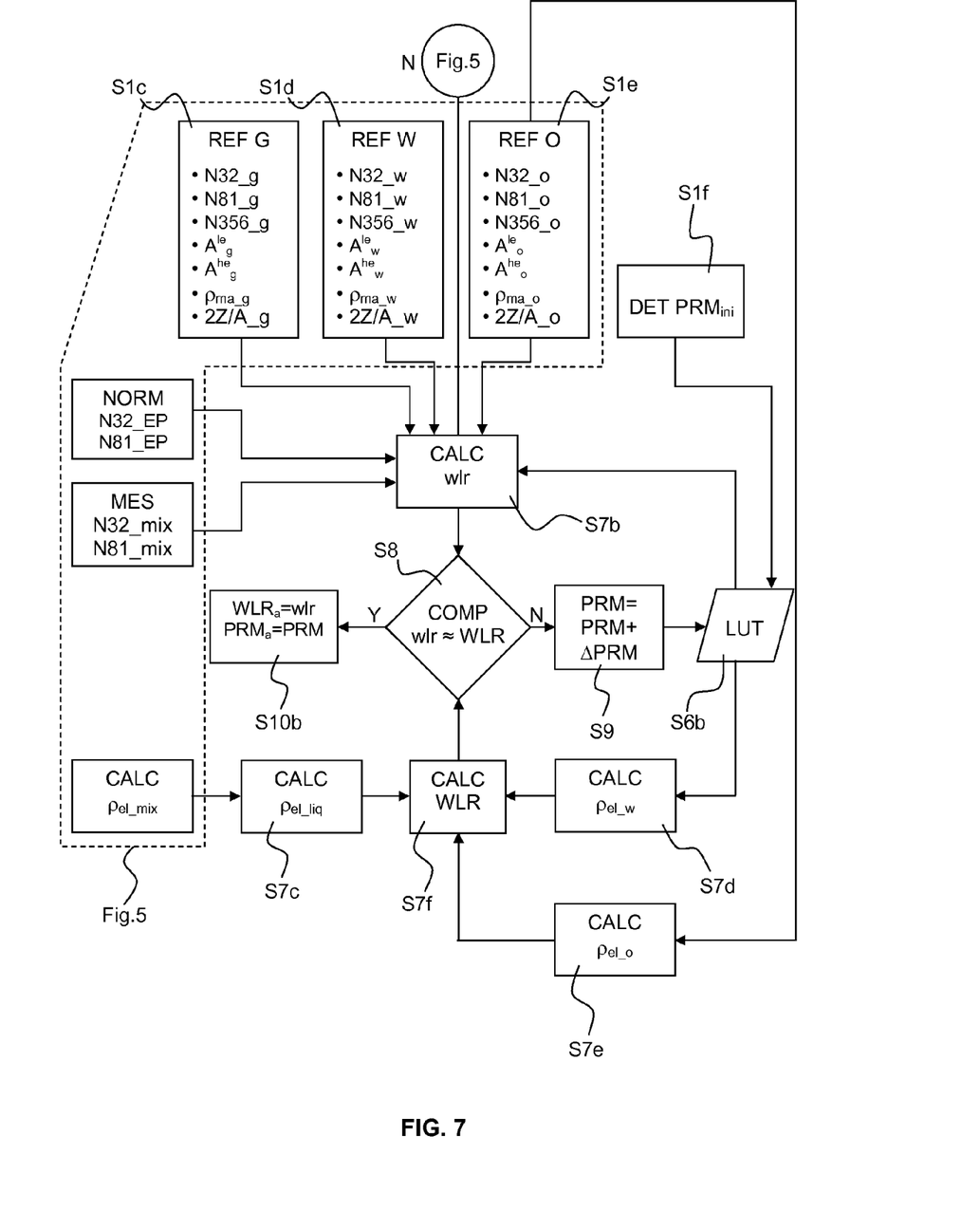

As a further alternative, the electronic density $\rho_{el\_mix}$ may be corrected with a factor depending on the atomic number Z and the mass number A of the multiphase fluid mixture prior to the comparison step. In this case:

$$\rho'_{ma\_mix} = \rho_{el\_mix} \times \left(\frac{A}{2Z}\right)_{mix},$$

and the fifth step S5 consists in comparing the mass density $\rho_{ma\_mix}$ and $\rho'_{ma\_mix}$. FIGS. 6 and 7 will now be described with a particular embodiment consisting in determining the water liquid ratio (WLR). However, the methodology is applicable with slight modification to the determination of other fluid mixture characteristic ratio, like the gas oil ratio (GOR) or the gas liquid ratio (GLR).

FIG. 6 is a diagram illustrating a method for determining a value of a water liquid ratio and a value of a parameter PRM affecting the water liquid ratio of a multiphase fluid mixture when the measurements made by the apparatus have been validated. In addition to the various reference measurements hereinbefore explained S1c, S1d and S1e, a further reference measurement DET $PRM_{ini}$ is performed (step S1f). The calibration DET $PRM_{ini}$ determines an initial value of the parameter affecting the water liquid ratio of the multiphase fluid mixture, for example the water salinity. Practically, all these reference measurements can be performed one time, for example using the multiphase fluid mixture produced by the hydrocarbon well where a characteristic ratio is to be monitored and by means of the measuring apparatus of the invention and other compositional analyses.

In a sixth step S6a, the theoretical mass attenuation coefficient values at 32 keV $A^{le}_w[P_{ini}]$ and at 81 keV $A^{he}_w[P_{ini}]$ as function of the parameter can be obtained from a look-up table LUT.

For example, in the case of salinity composition $PRM_{ini}=S_{ini}$, the values $A^{le}_w[S_{ini}]$ and $A^{he}_w[S_{ini}]$ may be obtained from National Institute of Standards and Technologies NIST tables. The input to the NIST mass attenuation calculator (web site www.nist.org) is the composition of the solution (salt or mixture) and fractional weight of each constituent. A transfer function is used to compute effective mass attenuation coefficients. Alternatively, these attenuations may be calculated.

In a seventh step S7a, the water liquid ratio is calculated CALC wlr. This determination is based on the initial value of the parameter affecting the water liquid ratio, the various reference values and the count rates measurements N32_mix and N81_mix for the determination of the mass density (See FIG. 5).

More precisely, the attenuations $A^{le}_{mix}$ and $A^{he}_{mix}$ are calculated at 32 keV and 81 keV:

$$A^{le}_{mix} = \ln\left(\frac{N32\_mix}{N32\_EP}\right) \text{ and}$$

$$A^{he}_{mix} = \ln\left(\frac{N81\_mix}{N81\_EP}\right).$$

Then, the water liquid ratio calculated from the count rates in the energy windows at 32 keV and 81 keV is calculated:

$$wlr = f(A^{le}_{mix}, A^{he}_{mix}, A^{le}_{w}[PRM], A^{ie}_{i}, A^{he}_{o}).$$

When measurements made by the apparatus have been validated (branch Y of FIG. 5), the actual value of the water liquid ration $WLR_a$ and of the parameter $PRM_a$ (e.g. salinity S) is the above calculated water liquid ration wlr and the initial value of the parameter $PRM_{ini}$, respectively (Step S10a).

FIG. 7 is a diagram illustrating a method for determining a value of a water liquid ratio and a value of a parameter affecting the water liquid ratio of a multiphase fluid mixture when the measurements made by the apparatus have not been validated. The various reference measurements REF G, EF W, REF O and DET $PRM_{ini}$ are still performed (first steps S1c, S1d, S1e and S1f described in relation with FIGS. 5 and 6).

Subsequently, a first water liquid ratio wlr value is obtained from the measurement at 32 keV and 81 keV for an initial value of the parameter $PRM_{ini}$ as described in relation with FIG. 6.

Concomitantly, a second water liquid ratio value is obtained from the measurement at 356 keV for an initial value of the parameter $PRM_{ini}$.

Following the electronic density $\rho_{el\_mix}$ calculation as described hereinbefore in connection with FIG. 5, the electronic density of the liquid fraction $\rho_{el\_liq}$, water $\rho_{el\_w}$ and oil $\rho_{el\_o}$ are calculated (Step S7c, S7d and S7e, respectively). More precisely, the electronic density of liquid fraction is given by:

$$\rho_{el\_liq} = \frac{\rho_{el\_mix} - (\rho_{el\_g} \times \alpha_g)}{1 - \alpha_g},$$

where $\alpha_g$ is the gas fraction and $\rho_{el\_g}$ is the electronic density of gas.

The volume fraction of each phase of the multiphase fluid mixture is determined with the measuring apparatus as described in the document WO 99/10712 ($\rho_{mix} = \alpha_g \rho_g + \alpha_o \rho_o + \alpha_w \rho_w$).

The electronic density of the oil fraction is calculated (Step S7e) by:

$$\rho_{el\_o} = \rho_{ma\_o} \times \left(\frac{2Z}{A}\right)_{oil}$$

The electronic density of water is calculated (Step S7d) by:

$$\rho_{el\_w}[PRM] = \rho_{ma\_w}[PRM] \times \left(\frac{2z[PRM]}{A[PRM]}\right)_w,$$

where the mass density of water affected by the parameter PRM is obtained from the look-up table LUT (Step S6b).

Then, the water liquid ratio calculated from the energy peak at 356 keV is calculated (Step S7e) by:

$$WLR = \frac{\rho_{el\_liq} - \rho_{el\_o}}{\rho_{el\_w}[PRM] - \rho_{el\_o}}$$

Subsequently, in the eighth step S8, the value of the water liquid ratio WLR calculated from the energy peak at 356 keV is compared to the water liquid ratio wlr calculated from the energy peaks at 32 keV and 81 keV. The comparison of the two water liquid ratio values enables identifying changes in water composition since the time when the reference measurements were acquired.

When the two water liquid ratio values wlr and WLR are not equal (taking into account the uncertainties associated with the calculated water liquid ratio values), the parameter PRM is changed by incrementing the parameter PRM=PRM+ΔPRM (Step S9). Subsequently, the steps S6b (look-up table), S7b (CALC wlr), S7d (CALC $\rho_{el\_w}$), S7e (CALC WLR) are repeated with the new value of the parameter PRM.

When the two water liquid ratio values wlr and WLR are equal (taking into account the uncertainties associated with the calculated water liquid ratio values), these two water liquid ratio values give the actual water liquid ratio of the fluid mixture $WLR_a$ and the parameter PRM is equal to the actual parameter value $PRM_a$ (Step S10b). In the example of salinity as a parameter affecting the water liquid ratio, a new mixture brine salinity is used to back calculate the new water liquid ratio and salinity by simulating a variation of the brine salinity varying from fresh water up to saturation (or by the mixing ratio of two different brines containing different salt species).

Figure 8:
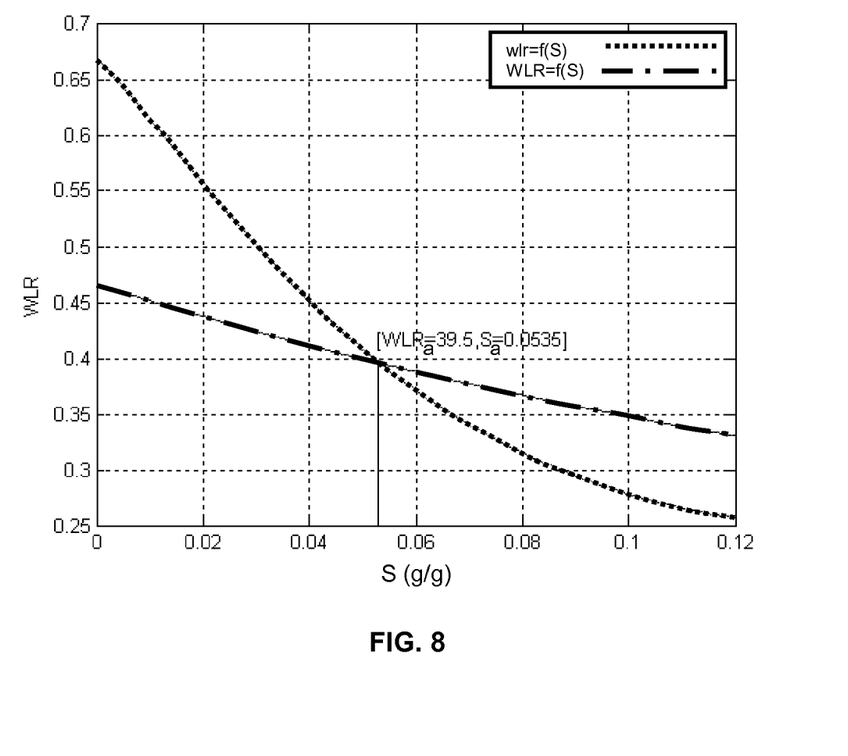
FIG. 8 is a graphic illustrating the method for determining a corrected value of a water liquid ratio and a corrected value of a parameter (example of NaCl salinity) affecting the water liquid ratio of a multiphase fluid mixture according to the invention.

FIG. 8 is a graphic illustrating the method for determining a corrected value of a water liquid ratio and a corrected value of a parameter affecting the water liquid ratio of a multiphase fluid mixture according to the invention.

In this example, the initial water liquid ratio is 40.8% with a measured initial water salinity of 0.052 g/g. The curve wlr=f(S) computed with 32 keV and 81 keV energy windows is compared to the curve WLR=f(S) computed with 356 keV energy window. These two curves cross at the same point WLR=wlr=39.5% for a computed salinity of S=0.0535 g/g.

The accuracy of the method depends on the amount of water present in the multiphase fluid mixture. The salinity can be reasonably determined with accuracy typically varying from +/−5% to +/−10% with the amount of water varying from 100% to 20%, respectively. The water liquid ratio can be reasonably determined with a typical accuracy of +/−5%, regardless of the salinity.

In the application example of FIG. 4, an operator can use the information of the water liquid ratio and parameter (e.g. salinity) to control the injection of the water into the injector well. A selective injection will allow an improved flushing of the reservoir portion in the vicinity of the producer well, thus improving the production by leaving less oil in the concerned reservoir portion.

Final Remarks

The hereinbefore described invention has been described with reference to a particular example where salinity affects the water liquid ratio. It is to be emphasized that the invention is not limited to a particular salt e.g. NaCl. The invention is applicable when the water liquid ratio is affected by any kind of salt, e.g. KCl, $CaCl_2$, $MgSO_4$, etc. . . . , or combination of different salt species. Furthermore, the invention is not limited to salinity, the invention can be similarly applied when any other parameters (for example $H_2S$, $CO_2$, Sulphur, etc. . . . ) may have an influence on the multiphase fluid mixture. Finally, the hereinbefore described invention is not limited to the water liquid ratio as other fluid mixture characteristic ratio (e.g. GOR, GLR) may be used in hydrocarbon well applications.

Though, a particular application of the invention to on-shore hydrocarbon well applications has been described, it will be apparent to a person skilled in the art that the invention is also applicable to off-shore hydrocarbon well applications.

It will be further apparent to a person skilled in the art that the Barium isotope source is an example and that other gamma or X-Ray sources may be appropriate, for example other chemical source or X-Ray producing apparatus (e.g. X-Ray tube).

The drawings and their description hereinbefore illustrate rather than limit the invention.

Any reference sign in a claim should not be construed as limiting the claim. The word "comprising" does not exclude the presence of other elements than those listed in a claim. The word "a" or "an" preceding an element does not exclude the presence of a plurality of such element.

The invention claimed is:

1. A method for controlling the quality of a mass density measurement of a multiphase fluid mixture (FM) comprising a plurality of fluid fractions and a plurality of constituting elements, the method comprising the steps of:

submitting a measuring pipe (3) to a flux of high energy photons and measuring count rates, the measuring pipe being arranged to let the photons pass through the multiphase fluid mixture, determining (S3a) a mass density ($\rho_{ma\_mix}$) of the multiphase fluid mixture based on count rate measurements (S2a, S2b) in a first (E32) and second (E81) energy window, the first (E32) and second (E81) energy windows being chosen so that the measurements in said energy windows are mainly sensitive to the fluid fractions, wherein the method further comprises the steps of:

determining (S4) an electronic density ($\rho_{el\_mix}$) of the multiphase fluid mixture based on count rate measurements (S2c) in a third energy window (E356), the third energy window (E356) being chosen so that the measurements in the third energy window (E356) are substantially sensitive to the density of the constituting elements, and comparing (S5) the electronic density ($\rho_{el\_mix}$) to the mass density ($\rho_{ma\_mix}$) of the multiphase fluid mixture, one of said densities being corrected with a factor depending on the atomic number (Z) and the mass number (A) of the multiphase fluid mixture prior to comparison, a difference between both densities indicating the quality of the mass density measurement of the multiphase fluid mixture.

2. The method for controlling the quality of a multiphase fluid mixture density measurement according to claim 1, wherein determining the mass density ($\rho_{ma\_mix}$) comprises:

measuring (S1a, S2a) a first (N32_EP) and a second (N32_mix) count rates in the first energy window (E32) when the measuring pipe is empty and when the multiphase fluid mixture is passed through the measuring pipe, respectively, measuring (S1a, S2b) a first (N81_EP) and a second (N81_mix) count rates in the second energy window (E81) when the measuring pipe is empty and when the multiphase fluid mixture is passed through the measuring pipe, respectively, and calculating (S3a) the mass density ($\rho_{ma\_mix}$) of the multiphase fluid mixture based on the first (N32_EP, N81_EP) and second (N32_mix, N81_mix) count rates in the first (E32) and second (E81) energy windows.

3. The method for controlling the quality of a multiphase fluid mixture density measurement according to claim 2, wherein determining the electronic density ($\rho_{el\_mix}$) comprises:

measuring (S1b, S2c) a first (N356_EP) and a second (N356_mix) count rates in the third energy window (E356) when the measuring pipe is empty and when the multiphase fluid mixture is passed through the measuring pipe, respectively, and calculating (S4) the electronic density ($\rho_{el\_mix}$) of the multiphase fluid mixture based on the first (N356_EP) and second (N356_mix) count rates in the third energy window (E356), and a measuring pipe geometry dependent factor (K).

4. A method for determining an actual value of a fluid mixture characteristic ratio ($WLR_a$) and an actual value of a parameter ($PRM_a$) affecting the characteristic ratio of a multiphase fluid mixture (FM), the multiphase fluid mixture comprising a plurality of fluid fractions, at least one fraction density being affected by the actual value of the parameter, the method comprising the steps of:

a) an initial reference measurement step comprising:

determining (S1f) an initial value of the parameter affecting the characteristic ratio of the multiphase fluid mixture, determining (S1c, S1d, S1e) reference values for each phase of the multiphase fluid mixture by submitting the measuring pipe to a flux of photons and measuring count rates, each phase being passed one at a time in the measuring pipe during the initial reference measurement step, b) a measuring step comprising:

applying (S3a, S3b, S4, S5) the method for controlling the quality of a mass density measurement of the multiphase fluid mixture according to any one of claims 1 to 3, c) when the quality is acceptable, a first characteristic ratio determination step (S7a, S10a) comprising determining the actual value of the characteristic ratio based on the initial value of the parameter affecting the characteristic ratio, the reference values and the mass density measurement, and d) when the quality is unacceptable, a second characteristic ratio determination step comprising:

determining (S7c, S7d, S7e, S7f) a first value (WLR) of the characteristic ratio based on the electronic density ($\rho_{el\_mix}$) of the multiphase fluid mixture, an electronic density ($\rho_{el\_liq}$) of a first fraction, an electronic density ($\rho_{el\_w}$) of a second fraction that is affected by the parameter, determining (S7b) a second value (wlr) of the characteristic ratio based on the value of the parameter affecting the characteristic ratio, the reference values and the mass density measurement, comparing (S8) the first (WLR) to the second (wlr) values of the characteristic ratio, applying a variation (S9) to the parameter (PRM) by incrementing the parameter (PRM=PRM+ΔPRM) when the first value (WLR) of the characteristic ratio is not substantially equal to the second value (wlr) of the characteristic ratio, and repeating the determination of the first and second value of the characteristic ratio based on the incremented parameter, and determining (S10b) the actual value (WLR$_a$) of the characteristic ratio and the actual value of the parameter (PRM$_a$) affecting the characteristic ratio when the first value (WLR) of the characteristic ratio is substantially equal to the second value (wlr) of the characteristic ratio.

5. The method for determining an actual value of a characteristic ratio and a parameter according to claim 4, wherein the characteristic ratio may be the water liquid ratio, the gas oil ratio, or the gas liquid ratio.

6. The method for determining an actual value of a characteristic ratio and a parameter according to claim 4, wherein the density ($\rho_{el\_w}$) of the fraction affected by the parameter (PRM) is obtained (S6b) from a look-up table (LUT).

7. The method for determining an actual value of a characteristic ratio and a parameter according to claim 4, wherein the parameter (PRM) is the water salinity.

8. A measuring apparatus comprising a measuring pipe (2, 3, 4, 5) arranged to let pass a multiphase fluid mixture, a source (6) emitting high energy photons into a plurality of energy levels though the measuring pipe, a detector (7) of photons receiving the photons attenuated by the multiphase fluid mixture (FM), and an electronic arrangement (8) coupled to the detector, wherein the electronic arrangement comprises a processor and a memory arranged to perform the determination and calculation steps of the method according to claims 1, 2, 3, 4, 5, 6 or 7.

9. The measuring apparatus according to claim 8, wherein the source (6) is a Barium 133 gamma source.

10. The measuring apparatus according to claim 8, wherein the source (6) is an X-Ray producing apparatus.

* * * * *